(12) United States Patent
MacMillan et al.

(10) Patent No.: US 7,265,249 B2
(45) Date of Patent: Sep. 4, 2007

(54) ENANTIOSELECTIVE ALPHA-FLUORINATION OF ALDEHYDES USING CHIRAL ORGANIC CATALYSTS

(75) Inventors: David W. C. MacMillan, Pasadena, CA (US); Teresa D. Beeson, Pasadena, CA (US)

(73) Assignee: California Institute of Technology, Pasadena, CA (US)

( * ) Notice: Subject to any disclaimer, the term of this patent is extended or adjusted under 35 U.S.C. 154(b) by 57 days.

(21) Appl. No.: 11/334,997

(22) Filed: Jan. 18, 2006

(65) Prior Publication Data

US 2006/0189830 A1 Aug. 24, 2006

Related U.S. Application Data

(60) Provisional application No. 60/644,549, filed on Jan. 18, 2005, provisional application No. 60/668,533, filed on Apr. 5, 2005.

(51) Int. Cl.
*C07C 45/63* (2006.01)
(52) U.S. Cl. ...................... 568/426; 568/449
(58) Field of Classification Search ............ None
See application file for complete search history.

(56) References Cited

U.S. PATENT DOCUMENTS

| | | | | |
|---|---|---|---|---|
| 5,003,074 | A | | 3/1991 | Allmendinger et al. ...... 548/206 |
| 5,081,249 | A | * | 1/1992 | Umemoto .................... 546/294 |
| 5,086,178 | A | * | 2/1992 | Banks .......................... 544/351 |
| 5,403,957 | A | | 4/1995 | Wagner et al. ................ 564/82 |
| 5,478,946 | A | | 12/1995 | Murad et al. ................ 548/215 |
| 5,552,533 | A | | 9/1996 | Poss et al. ................... 536/7.2 |
| 6,307,057 | B1 | | 10/2001 | MacMillan et al. ...... 548/316.4 |
| 6,517,137 | B2 | * | 2/2003 | Kiester et al. ............. 296/39.2 |
| 6,534,434 | B2 | * | 3/2003 | MacMillan et al. ......... 502/167 |

OTHER PUBLICATIONS

Beeson and MacMillan, "Enantioselective organocatalytic α-fluorination of aldehydes," J. Am. Chem. Soc. (2005) 127:8826-8828.
Hamashima et al., "An efficient catalytic enantioselective fluorination of β-ketophosphonates using chiral palladium complexes," Tetrahedron Lett. (2005) 46:1447-1450.
Kim and Park, "Catalytic enantioselective fluorination of β-ketoesters by phase-transfer catalysis using chiral quaternary ammonium salts," Org. Lett. (2002) 4:545-547.
Ma and Cahard., "Copper (II) triflate-bis(oxazoline)-catalysed enantioselective electrophilic fluorination of β-ketoesters," Tetrahedron Asymm. (2004) 15:1007-1011.
Purrington et al., "Preparation of α-fluoroaldehydes and α-fluoroketones using dilute fluorine," Tetrahedron Lett. (1986) 27:2715-2716.
Shibata et al., "First enantio-flexibe fluorination reaction using metal-bis(oxazoline) complexes," Synlett (2004) 10:1703-1706.
Stavber and Zupan, "Selectfluor™ F-TEDA-BF$_4$ as a versatile mediator or catalyst in organic chemistry," Acta Chim. Slov. (2005) 52:13-26.
Steiner et al., "Direct asymmetric α-fluorination of aldehydes," Angew. Chem. Intl. Ed. (2005) 44(24) p. 3706-3710.
Differding et al., "New fluorinating reagents—1. The first enantioselective fluorination reaction," Tetrahedron Lett. (1988) 29:6087-6090.

* cited by examiner

*Primary Examiner*—Sikarl A. Witherspoon
(74) *Attorney, Agent, or Firm*—Dianne E. Reed; Mintz Levin Cohn Ferris Glovsky and Popeo PC

(57) ABSTRACT

Nonmetallic, chiral organic catalysts are used to catalyze enantioselective fluorination of enolizable aldehydes. Reaction systems composed of an enolizable aldehyde, an electrophilic fluorination reagent, and a nonmetallic chiral catalyst in the form of an imidazolidinone salt are also provided.

20 Claims, No Drawings

ENANTIOSELECTIVE ALPHA-FLUORINATION OF ALDEHYDES USING CHIRAL ORGANIC CATALYSTS

CROSS-REFERENCE TO RELATED APPLICATIONS

This application claims priority under 35 U.S.C. §119(e)(1) to provisional U.S. Patent Application Ser. Nos. 60/644,549, filed Jan. 18, 2005, and 60/668,533, filed Apr. 5, 2005. The disclosures of the aforementioned applications are incorporated by reference in their entireties.

TECHNICAL FIELD

This invention relates generally to catalysis of enantioselective reactions, and more particularly relates to enantioselective reactions involving the use of chiral organic compounds to catalyze reactions of aldehydes. The invention has utility in the fields of catalysis and organic synthesis, including organocatalysis and chiral chemistry.

BACKGROUND

Within the realm of drug design, the stereospecific incorporation of fluorine substituents is a powerful and widely employed tactic to circumvent metabolism issues arising from in vivo C—H bond oxidation. On this basis, the catalytic production of carbon-fluorine stereogenicity has become a methodological goal of central importance to practitioners of chemical and pharmaceutical synthesis. Surprisingly, however, catalytic methods for the asymmetric construction of C—F bonds are rare, the majority involving α-substituted β-keto ester substrates that are structurally precluded from product epimerization (see Hamashima et al. (2005) *Tetrahedron Lett.* 46:1447; Shibara et al. (2004) *Snylett.* 1703; Ma et al. (2004) *Tetrahedron Asym.* 1007; Kim (2002) *Org. Lett.* 4:545). Alpha-fluoro aldehydes have been generally recognized as unstable compounds, insofar as decomposition is often noted upon purification, e.g., using column purification or distillation. See, e.g., Purrington et al. (1986) *Tet. Lett.* 27:2715-16. In addition, methods for halogenating aldehydes and ketones with bromine, chlorine, and iodine are not successful when fluorine is used.

There is, accordingly, a need in the art for an improved enantioselective fluorination method. An ideal method would enable rapid and enantiocontrolled C—F bond formation using stable, inexpensive reagents and catalysts that are inert to product epimerization and readily allow the fluorinated compound to be further functionalized.

SUMMARY OF THE INVENTION

The invention is directed to the aforementioned need in the art, and provides a new technique for effecting enantioselective fluorination. The method involves contacting an aldehyde with a fluorination reagent in the presence of a chiral secondary amine that serves as the reaction catalyst. The catalyst may be readily synthesized from inexpensive, commercially available reagents, is compatible with aerobic conditions, and provides the desired enantioselective fluorination products in high yield with a high level of enantioselectivity.

In a first aspect of the invention, then, a method is provided for carrying out an enantioselective fluorination reaction by contacting an enolizable aldehyde with a fluorine source in the presence of a catalytically effective amount of a nonmetallic chiral catalyst containing a Group 15 or Group 16 heteroatom. Any enolizable aldehyde may serve as the reaction substrate, meaning that the aldehyde may be substituted with one or more nonhydrogen substituents (provided that the substituents not interfere with the enantioselective fluorination reaction), so long as the α-carbon of the aldehyde contains an enolizable hydrogen atom.

Generally, the fluorine source is an electrophilic fluorination reagent such as "NFSi" (N-fluorobenzenesulfonimide), the enolizable aldehyde has the structure of formula (I)

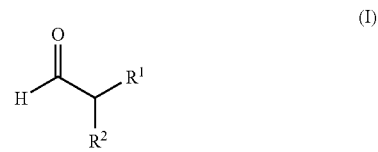

in which $R^1$ and $R^2$ are independently selected from hydrogen, hydrocarbyl, substituted hydrocarbyl, heteroatom-containing hydrocarbyl, substituted heteroatom-containing hydrocarbyl, and functional groups, and the nonmetallic chiral catalyst is a salt of a secondary amine, for instance an imidazolidinone salt having the structure of formula (III) or (IV)

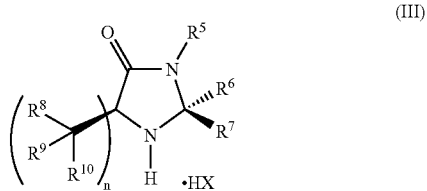

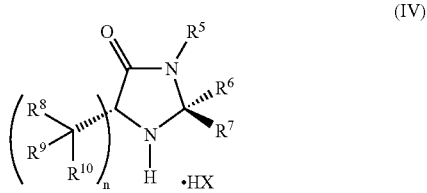

wherein:

$R^5$ is selected from hydrocarbyl, substituted hydrocarbyl, heteroatom-containing hydrocarbyl, and substituted heteroatom-containing hydrocarbyl;

$R^6$ and $R^7$ are independently selected from hydrocarbyl, substituted hydrocarbyl, heteroatom-containing hydrocarbyl, substituted heteroatom-containing hydrocarbyl, and functional groups;

$R^8$ is selected from hydrogen, halo, hydroxyl, hydrocarbyl, substituted hydrocarbyl, heteroatom-containing hydrocarbyl, substituted heteroatom-containing hydrocarbyl;

$R^9$ is selected from hydrogen, halo, hydrocarbyl, substituted hydrocarbyl, heteroatom-containing hydrocarbyl, substituted heteroatom-containing hydrocarbyl;

$R^{10}$ is a cyclic group, either unsubstituted or substituted with 1 to 4 non-hydrogen substituents and containing zero to 3 heteroatoms;

HX is a Brönsted acid; and n is zero or 1.

In another aspect of the invention, a reaction system is provided which contains an enolizable aldehyde, an electrophilic fluorination reagent, and the aforementioned chiral catalyst. It will be appreciated that the reaction system gives rise to a reaction product in the form of an aldehyde bearing a fluorine atom at the alpha position.

In contrast to previously known synthetic fluorination methods, the invention provides an operationally simple, organocatalytic technique for the stereospecific incorporation of fluorine substituents in a wide variety of molecular structures using a commercially available and/or readily synthesized fluorination reagent and catalyst.

DETAILED DESCRIPTION OF THE PREFERRED EMBODIMENTS

Unless otherwise indicated, the invention is not limited to specific molecular structures, substituents, synthetic methods, reaction conditions, or the like, as such may vary. It is also to be understood that the terminology used herein is for the purpose of describing particular embodiments only and is not intended to be limiting.

As used in the specification and the appended claims, the singular forms "a," "an," and "the" include plural referents unless the context clearly dictates otherwise. Thus, for example, reference to "a catalyst" includes a single catalyst as well as a combination or mixture of two or more catalysts, reference to "a substituent" encompasses a single substituent as well as two or more substituents, and the like.

In this specification and in the claims that follow, reference will be made to a number of terms, which shall be defined to have the following meanings:

The term "alkyl" as used herein refers to a linear, branched, or cyclic saturated hydrocarbon group typically although not necessarily containing 1 to about 24 carbon atoms, preferably 1 to about 12 carbon atoms, such as methyl, ethyl, n-propyl, isopropyl, n-butyl, isobutyl, t-butyl, octyl, decyl, and the like, as well as cycloalkyl groups such as cyclopentyl, cyclohexyl and the like. Generally, although again not necessarily, alkyl groups herein contain 1 to about 12 carbon atoms. The term "lower alkyl" intends an alkyl group of 1 to 6 carbon atoms, and the specific term "cycloalkyl" intends a cyclic alkyl group, typically having 4 to 8, preferably 5 to 7, carbon atoms. The term "substituted alkyl" refers to alkyl substituted with one or more substituent groups, and the terms "heteroatom-containing alkyl" and "heteroalkyl" refer to alkyl in which at least one carbon atom is replaced with a heteroatom. If not otherwise indicated, the terms "alkyl" and "lower alkyl" include linear, branched, cyclic, unsubstituted, substituted, and/or heteroatom-containing alkyl and lower alkyl, respectively.

The term "alkylene" as used herein refers to a difunctional linear, branched, or cyclic alkyl group, where "alkyl" is as defined above.

The term "alkenyl" as used herein refers to a linear, branched, or cyclic hydrocarbon group of 2 to about 24 carbon atoms containing at least one double bond, such as ethenyl, n-propenyl, isopropenyl, n-butenyl, isobutenyl, octenyl, decenyl, tetradecenyl, hexadecenyl, eicosenyl, tetracosenyl, and the like. Preferred alkenyl groups herein contain 2 to about 12 carbon atoms. The term "lower alkenyl" intends an alkenyl group of 2 to 6 carbon atoms, and the specific term "cycloalkenyl" intends a cyclic alkenyl group, preferably having 5 to 8 carbon atoms. The term "substituted alkenyl" refers to alkenyl substituted with one or more substituent groups, and the terms "heteroatom-containing alkenyl" and "heteroalkenyl" refer to alkenyl in which at least one carbon atom is replaced with a heteroatom. If not otherwise indicated, the terms "alkenyl" and "lower alkenyl" include linear, branched, cyclic, unsubstituted, substituted, and/or heteroatom-containing alkenyl and lower alkenyl, respectively.

The term "alkenylene" as used herein refers to a difunctional linear, branched, or cyclic alkenyl group, where "alkenyl" is as defined above.

The term "alkynyl" as used herein refers to a linear or branched hydrocarbon group of 2 to about 24 carbon atoms containing at least one triple bond, such as ethynyl, n-propynyl, and the like. Preferred alkynyl groups herein contain 2 to about 12 carbon atoms. The term "lower alkynyl" intends an alkynyl group of 2 to 6 carbon atoms. The term "substituted alkynyl" refers to alkynyl substituted with one or more substituent groups, and the terms "heteroatom-containing alkynyl" and "heteroalkynyl" refer to alkynyl in which at least one carbon atom is replaced with a heteroatom. If not otherwise indicated, the terms "alkynyl" and "lower alkynyl" include linear, branched, unsubstituted, substituted, and/or heteroatom-containing alkynyl and lower alkynyl, respectively.

The term "alkoxy" as used herein intends an alkyl group bound through a single, terminal ether linkage; that is, an "alkoxy" group may be represented as —O-alkyl where alkyl is as defined above. A "lower alkoxy" group intends an alkoxy group containing 1 to 6 carbon atoms. Analogously, "alkenyloxy" and "lower alkenyloxy" respectively refer to an alkenyl and lower alkenyl group bound through a single, terminal ether linkage, and "alkynyloxy" and "lower alkynyloxy" respectively refer to an alkynyl and lower alkynyl group bound through a single, terminal ether linkage.

The term "aryl" as used herein, and unless otherwise specified, refers to an aromatic substituent containing a single aromatic ring or multiple aromatic rings that are fused together, directly linked, or indirectly linked (such that the different aromatic rings are bound to a common group such as a methylene or ethylene moiety). Preferred aryl groups contain 5 to 24 carbon atoms, and particularly preferred aryl groups contain 5 to 14 carbon atoms. Exemplary aryl groups contain one aromatic ring or two fused or linked aromatic rings, e.g., phenyl, naphthyl, biphenyl, diphenylether, diphenylamine, benzophenone, and the like. "Substituted aryl" refers to an aryl moiety substituted with one or more substituent groups, and the terms "heteroatom-containing aryl" and "heteroaryl" refer to aryl substituents in which at least one carbon atom is replaced with a heteroatom, as will be described in further detail infra.

The term "aryloxy" as used herein refers to an aryl group bound through a single, terminal ether linkage, wherein "aryl" is as defined above. An "aryloxy" group may be represented as —O-aryl where aryl is as defined above. Preferred aryloxy groups contain 5 to 24 carbon atoms, and particularly preferred aryloxy groups contain 5 to 14 carbon atoms. Examples of aryloxy groups include, without limitation, phenoxy, o-halo-phenoxy, m-halo-phenoxy, p-halo-phenoxy, o-methoxy-phenoxy, m-methoxy-phenoxy, p-methoxy-phenoxy, 2,4-dimethoxy-phenoxy, 3,4,5-trimethoxy-phenoxy, and the like.

The term "alkaryl" refers to an aryl group with an alkyl substituent, and the term "aralkyl" refers to an alkyl group with an aryl substituent, wherein "aryl" and "alkyl" are as defined above. Preferred alkaryl and aralkyl groups contain 6 to 24 carbon atoms, and particularly preferred alkaryl and aralkyl groups contain 6 to 16 carbon atoms. Alkaryl groups include, for example, p-methylphenyl, 2,4-dimethylphenyl, p-cyclohexylphenyl, 2,7-dimethylnaphthyl, 7-cyclooctyl-naphthyl, 3-ethyl-cyclopenta-1,4-diene, and the like. Examples of aralkyl groups include, without limitation, benzyl, 2-phenyl-ethyl, 3-phenyl-propyl, 4-phenyl-butyl, 5-phenyl-pentyl, 4-phenylcyclohexyl, 4-benzylcyclohexyl, 4-phenylcyclohexylmethyl, 4-benzylcyclohexylmethyl, and the like. The terms "alkaryloxy" and "aralkyloxy" refer to substituents of the formula —OR wherein R is alkaryl or aralkyl, respectively, as just defined.

The terms "cyclic" and "ring" refer to alicyclic or aromatic groups that may or may not be substituted and/or heteroatom containing, and that may be monocyclic, bicyclic, or polycyclic. The term "alicyclic" is used in the conventional sense to refer to an aliphatic cyclic moiety, as opposed to an aromatic cyclic moiety, and may be monocyclic, bicyclic or polycyclic.

The terms "halo" and "halogen" are used in the conventional sense to refer to a chloro, bromo, fluoro or iodo substituent.

"Hydrocarbyl" refers to univalent hydrocarbyl radicals containing 1 to about 30 carbon atoms, preferably 1 to about 24 carbon atoms, most preferably 1 to about 12 carbon atoms, including linear, branched, cyclic, saturated and unsaturated species, such as alkyl groups, alkenyl groups, aryl groups, and the like. The term "lower hydrocarbyl" intends a hydrocarbyl group of 1 to 6 carbon atoms, preferably 1 to 4 carbon atoms, and the term "hydrocarbylene" intends a divalent hydrocarbyl moiety containing 1 to about 30 carbon atoms, preferably 1 to about 24 carbon atoms, most preferably 1 to about 12 carbon atoms, including linear, branched, cyclic, saturated and unsaturated species. The term "lower hydrocarbylene" intends a hydrocarbylene group of 1 to 6 carbon atoms. "Substituted hydrocarbyl" refers to hydrocarbyl substituted with one or more substituent groups, and the terms "heteroatom-containing hydrocarbyl" and "heterohydrocarbyl" refer to hydrocarbyl in which at least one carbon atom is replaced with a heteroatom. Similarly, "substituted hydrocarbylene" refers to hydrocarbylene substituted with one or more substituent groups, and the terms "heteroatom-containing hydrocarbylene" and "heterohydrocarbylene" refer to hydrocarbylene in which at least one carbon atom is replaced with a heteroatom. Unless otherwise indicated, the term "hydrocarbyl" and "hydrocarbylene" are to be interpreted as including substituted and/or heteroatom-containing hydrocarbyl and hydrocarbylene moieties, respectively.

The term "heteroatom-containing" as in a "heteroatom-containing hydrocarbyl group" refers to a hydrocarbon molecule or a hydrocarbyl molecular fragment in which one or more carbon atoms is replaced with an atom other than carbon, e.g., nitrogen, oxygen, sulfur, phosphorus or silicon, typically nitrogen, oxygen or sulfur. Similarly, the term "heteroalkyl" refers to an alkyl substituent that is heteroatom-containing, the term "heterocyclic" refers to a cyclic substituent that is heteroatom-containing, the terms "heteroaryl" and heteroaromatic" respectively refer to "aryl" and "aromatic" substituents that are heteroatom-containing, and the like. It should be noted that a "heterocyclic" group or compound may or may not be aromatic, and further that "heterocycles" may be monocyclic, bicyclic, or polycyclic as described above with respect to the term "aryl." Examples of heteroalkyl groups include alkoxyaryl, alkylsulfanyl-substituted alkyl, N-alkylated amino alkyl, and the like. Examples of heteroaryl substituents include pyrrolyl, pyrrolidinyl, pyridinyl, quinolinyl, indolyl, pyrimidinyl, imidazolyl, 1,2,4-triazolyl, tetrazolyl, etc., and examples of heteroatom-containing alicyclic groups are pyrrolidino, morpholino, piperazino, piperidino, etc.

By "substituted" as in "substituted hydrocarbyl," "substituted alkyl," "substituted aryl," and the like, as alluded to in some of the aforementioned definitions, is meant that in the hydrocarbyl, alkyl, aryl, or other moiety, at least one hydrogen atom bound to a carbon (or other) atom is replaced with one or more non-hydrogen substituents. Examples of such substituents include, without limitation: functional groups referred to herein as "Fn," such as halo, hydroxyl, sulfhydryl, $C_1$-$C_{24}$ alkoxy, $C_2$-$C_{24}$ alkenyloxy, $C_2$-$C_{24}$ alkynyloxy, $C_5$-$C_{24}$ aryloxy, $C_6$-$C_{24}$ aralkyloxy, $C_6$-$C_{24}$ alkaryloxy, acyl (including $C_2$-$C_{24}$ alkylcarbonyl (—CO-alkyl) and $C_6$-$C_{24}$ arylcarbonyl (—CO-aryl)), acyloxy (—O-acyl, including $C_2$-$C_{24}$ alkylcarbonyloxy (—O—CO-alkyl) and $C_6$-$C_{24}$ arylcarbonyloxy (—O—CO-aryl)), $C_2$-$C_{24}$ alkoxycarbonyl (—(CO)—O-alkyl), $C_6$-$C_{24}$ aryloxycarbonyl (—(CO)—O-aryl), halocarbonyl (—CO)—X where X is halo), $C_2$-$C_{24}$ alkylcarbonato (—O—(CO)—O-alkyl), $C_6$-$C_{24}$ arylcarbonato (—O—(CO)—O-aryl), carboxy (—COOH), carboxylato (—COO$^-$), carbamoyl (—(CO)—NH$_2$), mono-($C_1$-$C_{24}$ alkyl)-substituted carbamoyl (—(CO)—NH($C_1$-$C_{24}$ alkyl)), di-($C_1$-$C_{24}$ alkyl)-substituted carbamoyl (—(CO)—N($C_1$-$C_{24}$ alkyl)$_2$), mono-($C_5$-$C_{24}$ aryl)-substituted carbamoyl (—(CO)—NH-aryl), di-($C_5$-$C_{24}$ aryl)-substituted carbamoyl (—(CO)—N($C_5$-$C_{24}$ aryl)$_2$), di-N—($C_1$-$C_{24}$ alkyl),N—($C_5$-$C_{24}$ aryl)-substituted carbamoyl, thiocarbamoyl (—(CS)—NH$_2$), mono-($C_1$-$C_{24}$ alkyl)-substituted thiocarbamoyl (—(CO)—NH($C_1$-$C_{24}$ alkyl)), di-($C_1$-$C_{24}$ alkyl)-substituted thiocarbamoyl (—(CO)—N($C_1$-$C_{24}$ alkyl)$_2$), mono-($C_5$-$C_{24}$ aryl)-substituted thiocarbamoyl (—(CO)—NH-aryl), di-($C_5$-$C_{24}$ aryl)-substituted thiocarbamoyl (—(CO)—N($C_5$-$C_{24}$ aryl)$_2$), di-N—($C_1$-$C_{24}$ alkyl),N—($C_5$-$C_{24}$ aryl)-substituted thiocarbamoyl, carbamido (—NH—(CO)—NH$_2$), cyano(—C≡N), cyanato (—O—C≡N), thiocyanato (—S—C≡N), formyl (—(CO)—H), thioformyl (—(CS)—H), amino (—NH$_2$), mono-($C_1$-$C_{24}$ alkyl)-substituted amino, di-($C_1$-$C_{24}$ alkyl)-substituted amino, mono-($C_5$-$C_{24}$ aryl)-substituted amino, di-($C_5$-$C_{24}$ aryl)-substituted amino, $C_2$-$C_{24}$ alkylamido (—NH—(CO)-alkyl), $C_6$-$C_{24}$ arylamido (—NH—(CO)-aryl), imino (—CR=NH where R=hydrogen, $C_1$-$C_{24}$ alkyl, $C_5$-$C_{24}$ aryl, $C_6$-$C_{24}$ alkaryl, $C_6$-$C_{24}$ aralkyl, etc.), $C_2$-$C_{20}$ alkylimino (—CR=N(alkyl), where R=hydrogen, $C_1$-$C_{24}$ alkyl, $C_5$-$C_{24}$ aryl, $C_6$-$C_{24}$ alkaryl, $C_6$-$C_{24}$ aralkyl, etc.), arylimino (—CR=N(aryl), where R=hydrogen, $C_1$-$C_{20}$ alkyl, $C_5$-$C_{24}$ aryl, $C_6$-$C_{24}$ alkaryl, $C_6$-$C_{24}$ aralkyl, etc.), nitro (—NO$_2$), nitroso (—NO), sulfo (—SO$_2$—OH), sulfonato (—SO$_2$—O$^-$), $C_1$-$C_{24}$ alkylsulfanyl (—S-alkyl; also termed "alkylthio"), $C_5$-$C_{24}$ arylsulfanyl (—S-aryl; also termed "arylthio"), $C_1$-$C_{24}$ alkylsulfinyl (—(SO)-alkyl), $C_5$-$C_{24}$ arylsulfinyl (—(SO)-aryl), $C_1$-$C_{24}$ alkylsulfonyl (—SO$_2$-alkyl), $C_5$-$C_{24}$ arylsulfonyl (—SO$_2$-aryl), boryl (—BH$_2$), borono (—B(OH)$_2$), boronato (—B(OR)$_2$ where R is alkyl or other hydrocarbyl), phosphono (—P(O)(OH)$_2$), phosphonato (—P(O)(O$^-$)$_2$), phosphinato (—P(O)(O$^-$)), phospho (—PO$_2$), and phosphino (—PH$_2$); and the hydrocarbyl moieties $C_1$-$C_{24}$ alkyl (preferably $C_1$-$C_{12}$ alkyl, more preferably $C_1$-$C_6$ alkyl), $C_2$-$C_{24}$ alkenyl (preferably $C_2$-$C_{12}$ alkenyl, more preferably $C_2$-$C_6$ alkenyl), $C_2$-$C_{24}$ alkynyl (preferably $C_2$-$C_{12}$ alkynyl, more preferably $C_2$-$C_6$ alkynyl), $C_5$-$C_{24}$ aryl (preferably $C_5$-$C_{14}$ aryl), $C_6$-$C_{24}$ alkaryl (preferably $C_6$-$C_{16}$ alkaryl), and $C_6$-$C_{24}$ aralkyl (preferably $C_6$-$C_{16}$ aralkyl).

In addition, the aforementioned functional groups may, if a particular group permits, be further substituted with one or more additional functional groups or with one or more hydrocarbyl moieties such as those specifically enumerated above. Analogously, the above-mentioned hydrocarbyl moieties may be further substituted with one or more functional groups or additional hydrocarbyl moieties such as those specifically enumerated.

"Optional" or "optionally" means that the subsequently described circumstance may or may not occur, so that the description includes instances where the circumstance occurs and instances where it does not. For example, the phrase "optionally substituted" means that a non-hydrogen substituent may or may not be present on a given atom, and, thus, the description includes structures wherein a non-hydrogen substituent is present and structures wherein a non-hydrogen substituent is not present.

The term "chiral" refers to a structure that does not have an improper rotation axis ($S_n$), i.e., it belongs to point group $C_n$ or $D_n$. Such molecules are thus chiral with respect to an axis, plane or center of asymmetry. Preferred "chiral" molecules herein are in enantiomerically pure form, such that a particular chiral molecule represents at least about 95 wt. % of the composition in which it is contained, more preferably at least about 99 wt. % of that composition.

The term "enantioselective" refers to a chemical reaction that preferentially results in one enantiomer relative to a second enantiomer, i.e., gives rise to a product of which a desired enantiomer represents at least about 50 wt. %. Preferably, in the enantioselective reactions herein, the desired enantiomer represents at least about 90 wt. % of the product, more preferably at least about 95 wt. % of the product, optimally at least about 95 wt. % of the product.

In the molecular structures herein, the use of bold and dashed lines to denote particular conformation of groups follows the IUPAC convention. A bond indicated by a broken line indicates that the group in question is below the general plane of the molecule as drawn (the "α" configuration), and a bond indicated by a bold line indicates that the group at the position in question is above the general plane of the molecule as drawn (the "β" configuration).

Accordingly, the invention provides a method for using organic catalysts to carry out an enantioselective fluorination reaction using an aldehyde as substrate, i.e., to provide a chiral fluorinated aldehyde in substantially enantiomerically pure form as an intermediate or final product.

Any enolizable aldehyde may be employed as the reaction substrate, meaning that the sole requirement of the aldehyde is that the α-carbon contain an enolizable hydrogen atom. The α-carbon may be substituted with one or two nonhydrogen substituents that may be the same or different, e.g., a hydrocarbyl, substituted hydrocarbyl, heteroatom-containing hydrocarbyl, or substituted heteroatom-containing hydrocarbyl group, or, in some cases, a functional group. Accordingly, the enolizable aldehyde may be represented by the structure of formula (I)

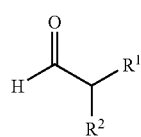

(I)

In which $R^1$ and $R^2$ are independently selected from hydrogen, hydrocarbyl, substituted hydrocarbyl, heteroatom-containing hydrocarbyl, substituted heteroatom-containing hydrocarbyl, and functional groups. Typically, $R^1$ and $R^2$ are independently selected from hydrogen, $C_1$-$C_{24}$ alkyl, substituted $C_1$-$C_{24}$ alkyl, $C_1$-$C_{24}$ heteroalkyl, substituted $C_1$-$C_{24}$ heteroalkyl, $C_5$-$C_{24}$ aryl, substituted $C_5$-$C_{24}$ aryl, $C_1$-$C_{24}$ heteroaryl, substituted $C_1$-$C_{24}$ heteroaryl, $C_6$-$C_{24}$ aralkyl, substituted $C_6$-$C_{24}$ aralkyl, $C_2$-$C_{24}$ heteroaralkyl, substituted $C_2$-$C_{24}$ heteroaralkyl, hydroxyl, $C_1$-$C_{24}$ alkoxy, sulfhydryl, and amino, and more typically $R^1$ and $R^2$ are independently selected from hydrogen, $C_1$-$C_{12}$ alkyl, substituted $C_1$-$C_{12}$ alkyl, $C_1$-$C_{12}$ heteroalkyl, substituted $C_1$-$C_{12}$ heteroalkyl, $C_5$-$C_{14}$ aryl, substituted $C_5$-$C_{14}$ aryl, $C_3$-$C_{14}$ heteroaryl, substituted $C_3$-$C_{14}$ heteroaryl, $C_6$-$C_{16}$ aralkyl, substituted $C_6$-$C_{16}$ aralkyl, $C_3$-$C_{16}$ heteroaralkyl, substituted $C_3$-$C_{16}$ heteroaralkyl, hydroxyl, sulfhydryl, and amino.

Preferred enolizable aldehydes contain one substituent at the α-carbon and may thus have the structure of formula (Ia)

(Ia)

(i.e., $R^2$ is H) wherein $R^1$ is selected from hydrocarbyl, substituted hydrocarbyl, heteroatom-containing hydrocarbyl, substituted heteroatom-containing hydrocarbyl, and functional groups, and is preferably selected from $C_1$-$C_{24}$ alkyl, substituted $C_1$-$C_{24}$ alkyl, $C_1$-$C_{24}$ heteroalkyl, substituted $C_1$-$C_{24}$ heteroalkyl, $C_5$-$C_{24}$ aryl, substituted $C_5$-$C_{24}$ aryl, $C_1$-$C_{24}$ heteroaryl, substituted $C_1$-$C_{24}$ heteroaryl, $C_6$-$C_{24}$ aralkyl, substituted $C_6$-$C_{24}$ aralkyl, $C_2$-$C_{24}$ heteroaralkyl, and substituted $C_2$-$C_{24}$ heteroaralkyl. Optimally, in this embodiment, $R^1$ is selected from $C_1$-$C_{12}$ alkyl, substituted $C_1$-$C_{12}$ alkyl, $C_1$-$C_{12}$ heteroalkyl, substituted $C_1$-$C_{12}$ heteroalkyl, $C_5$-$C_{14}$ aryl, substituted $C_5$-$C_{14}$ aryl, $C_3$-$C_{14}$ heteroaryl, substituted $C_3$-$C_{14}$ heteroaryl, $C_6$-$C_{16}$ aralkyl, substituted $C_6$-$C_{16}$ aralkyl, $C_3$-$C_{16}$ heteroaralkyl, and substituted $C_3$-$C_{16}$ heteroaralkyl.

The fluorine source is an electrophilic fluorination reagent, with preferred such fluorination reagents being those generally referred to as "N—F" type fluorinating compounds. See, e.g., U.S. Pat. No. 5,552,533. Illustrative of these types of fluorinating reagents are N-fluorobenzenesulfonimide (NFSi) and its derivatives (see U.S. Pat. No. 5,116,982), N-fluoromethanesulfonimide and its derivatives, N-fluoropyridinium pyridine heptafluorodiborate (NFPy), 1-chloromethyl-4-fluoro-1,4-diazoniabicyclo[2.2.2]octane bis(tetrafluoroborate) (F-TEDA) and other 1-alkyl-4-fluoro-1,4-diazoniabicyclo[2.2.2]octane salts and fluorinated diazabicycloalkane derivatives thereof (see U.S. Pat. No. 5,086,178), 1-hydroxyl-4-fluoro-1,4-diazoniabicyclo[2.2.2]octane bis(tetrafluoroborate) (NFTh), and other fluorinated derivatives thereof (see U.S. Pat. No. 5,459,267), N-alkyl-N-fluoro-p-toluenesulphonamides, N-fluoro-o-benzene-disulfonimide, N-fluoro-N-alkylsulfonamides, N-fluoropyridinium sulfonates (see U.S. Pat. No. 5,081,249), perfluoro-N-fluoro-N-(4-pyridyl)methanesulphonamide and various substituted N-fluoropyridinium salts. Further information concerning electrophilic fluorination reagents may be found, for example, in Murtagh (1992), "Further Progress on Electro-fluorination," Performance Chemicals, p 27; Furin, "New Fluorinating Agents in Organic Synthesis," eds. L. German and S. Zemskov, Springer Verlag, Berlin (1989); Umemoto et. al. (1990), "Power and Structure-Variable Fluorinating Agents. The N-Fluoropyridinium Salt System," J. Am. Chem. Soc. 112: 8563; and Differding et al. (1991), "N-Fluorobenzene-sulfonimide: A Practical Reagent for Electrophilic Fluorinations," Synthetic Letters 187. The preferred fluorinating agents are the fluorinated diazabicycloalkane compounds described in U.S. Pat. No. 5,086,178, the N-fluorobenzenesulfonimides described in U.S. Pat. No. 5,254,732, and the 1-substituted-4-fluoro-1,4-diazoniabicyclo[2.2.2]octane salts described in U.S. Pat. No. 5,459,267.

Exemplary fluorination reagents for use herein include, without limitation, N-fluorobenzenesulfonimide, N-fluoromethanesulfonimide, 1-chloromethyl-4-fluoro-1,4-diazoniabicyclo[2.2.2]octane bis(tetra-fluoroborate), 1-hydroxyl-4-fluoro-1,4-diazoniabicyclo[2.2.2]octane bis(tetrafluoroborate), and N-fluoropyridinium pyridine heptafluorodiborate.

The catalyst is a nonmetallic chiral catalyst containing a Group 15 or Group 16 heteroatom, e.g., nitrogen, oxygen, sulfur or phosphorus, and a preferred heteroatom is nitrogen. Oxygen-containing and sulfur-containing catalysts may be, for example, alcohols and thiols, respectively, while phosphorus-containing catalysts will generally be phosphines. Organic catalysts in which the heteroatom is a nitrogen atom may be a primary amine, a secondary amine or a nitrogen-containing polymer. Preferred amine catalysts, however, are secondary amines having the structure of formula (III)

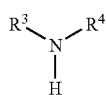

(III)

In formula (III), $R^3$ and $R^4$ are selected from the group consisting of hydrogen, hydrocarbyl (e.g., alkyl, alkenyl, alkynyl, aryl, alkaryl, alkaryl, etc.), substituted hydrocarbyl (e.g., substituted alkyl, alkenyl, alkynyl, aryl, alkaryl, alkaryl, etc.), heteroatom-containing hydrocarbyl (e.g., heteroatom-containing alkyl, alkenyl, alkynyl, aryl, alkaryl, alkaryl, etc.), and substituted heteroatom-containing hydrocarbyl (e.g., substituted heteroatom-containing alkyl, alkenyl, alkynyl, aryl, alkaryl, alkaryl, etc.), or $R^3$ and $R^4$ are taken together to form a substituted or unsubstituted ring structure optionally containing a further heteroatom in addition to the nitrogen atom shown in formula (III). When $R^3$ and $R^4$ are linked, the ring formed may be, for example, a five- or six-membered alicyclic or aromatic group, e.g., $R^3$ and $R^4$ may together form substituted or unsubstituted cyclopentyl, cyclohexyl, pyrrolidinyl, piperidinyl, morpholinyl, pyrrolyl, pyridinyl, pyrimidinyl, imidazolyl, or the like. Particularly preferred compounds are those wherein $R^3$ and $R^4$ are linked to form a 3- to 15-membered, optionally substituted cyclic moiety.

Representative of those catalysts which are particularly preferred in conjunction with the present invention is the imidazolidinone salt having the structure of formula (III) or (IV)

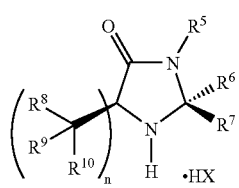

(III)

-continued

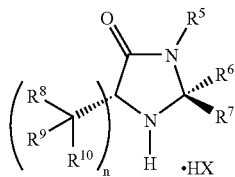

(IV)

wherein the various substituents are as follows:

In formulae (III) and (IV), $R^5$, $R^6$, and $R^7$ are independently selected from the group consisting of hydroxyl, sulfhydryl, amino, substituted amino, carboxyl, hydrocarbyl (e.g., alkyl, alkenyl, alkynyl, aryl, alkaryl, alkaryl, etc.), substituted hydrocarbyl (e.g., substituted alkyl, alkenyl, alkynyl, aryl, alkaryl, alkaryl, etc.), heteroatom-containing hydrocarbyl (e.g., heteroatom-containing alkyl, alkenyl, alkynyl, aryl, alkaryl, alkaryl, etc.), and substituted heteroatom-containing hydrocarbyl (e.g., substituted heteroatom-containing alkyl, alkenyl, alkynyl, aryl, alkaryl, alkaryl, etc.). Preferably, $R^5$, $R^6$, and $R^7$ are independently selected from the group consisting of hydroxyl, sulfhydryl, amino, substituted amino, carboxyl, alkyl, heteroalkyl, substituted alkyl, alkenyl, heteroalkenyl, substituted alkenyl, alkynyl, heteroalkynyl, substituted alkynyl, aryl, heteroaryl and substituted aryl. Most preferably, $R^5$, $R^6$, and $R^7$ are each lower alkyl, preferably methyl.

The substituents $R^8$ and $R^9$ may be independently hydrido or halo, or they may be selected from the aforementioned substituent possibilities given for $R^5$, $R^6$, and $R^7$. In a particularly preferred embodiment, $R^8$ and $R^9$ are hydrido. In addition, any two or more of $R^5$, $R^6$, $R^7$, $R^8$ and $R^9$ can be linked to form a cyclic group, typically through a hydrocarbylene, substituted hydrocarbylene, heteroatom-containing hydrocarbylene or substituted heteroatom-containing hydrocarbylene linkage.

The subscript "n" is 0 or 1, preferably 1.

The $R^{10}$ group is a cyclic moiety, and preferred $R^{10}$ groups are heterocyclic or aromatic. $R^{10}$ may or may not be substituted with the same or different substituents and suitable substituents are amino, halo, or any of the above-mentioned substituent possibilities given for $R^5$, $R^6$, and $R^7$. In a preferred embodiment, $R^{10}$ is an unsubstituted phenyl group.

Accordingly, one exemplary group of catalysts has the structure of formula (III) or (IV) wherein:

$R^5$ is selected from $C_1$-$C_{12}$ alkyl, substituted $C_1$-$C_{12}$ alkyl, $C_1$-$C_{12}$ heteroalkyl, substituted $C_1$-$C_{12}$ heteroalkyl, $C_5$-$C_{14}$ aryl, substituted $C_5$-$C_{14}$ aryl, $C_3$-$C_{14}$ heteroaryl, substituted $C_3$-$C_{14}$ heteroaryl, $C_6$-$C_{16}$ aralkyl, substituted $C_6$-$C_{16}$ aralkyl, $C_3$-$C_{16}$ heteroaralkyl, and substituted $C_3$-$C_{16}$ heteroaralkyl;

$R^6$ and $R^7$ are selected from $C_1$-$C_{12}$ alkyl and substituted $C_1$-$C_{12}$ alkyl;

n is 1;

$R^8$ and $R^9$ are hydrogen; and $R^{10}$ is $C_5$-$C_{14}$ aryl.

Particularly preferred catalysts within the aforementioned group are those wherein $R^5$, $R^6$, and $R^7$ are $C_1$-$C_{12}$ alkyl, $R^6$ and $R^7$ are the same, and $R^{10}$ is unsubstituted phenyl. Exemplary preferred catalysts are those wherein $R^5$, $R^6$, and $R^7$, i.e., (5R)- and (5S)-benzyl-2,2,3-trimethylimidazolidin-4-one hydrochloride.

The Brönsted acid HX, which provides the anion $X^-$, is generally although not necessarily selected from acids having a pKa of less than about 5. Combinations of Brönsted acids may also be used. Suitable acids include both organic and inorganic acids, e.g., hydrochloric acid, hydrobromic acid, perchloric acid, sulfurous acid, sulfuric acid, sulfonic acids (including alkyl and aryl sulfonic acids), phosphoric acid, phosphonic acids (including alkyl and aryl phosphonic acids), nitric acid, nitrous acid, chromic acid, methylsulfonic acid, triflic acid, acetic acid, haloacetic acids, benzoic acid, propionic acid, fumaric acid, maleic acid, succinic acid, salicylic acid, mixtures thereof and the like.

The imidazolidinone salt can be obtained commercially or synthesized using routine methodology known to those skilled in the art of synthetic organic chemistry and/or described in the pertinent texts and literature. The salt may be synthesized by admixing the imidazolidinone (in uncharged, free base form) with a Brönsted acid HX, at a desired molar ratio, generally in the range of approximately 1:100 to 100:1, typically about 1:10 to 10:1, preferably about 1:2 to 2:1. Alternatively, the components of the salt, i.e., the uncharged imidazolidinone and the Brönsted acid, may be combined just prior to or during the catalyzed reaction. In still another embodiment, the uncharged imidazolidinone may be combined with at least one salt $M^{+q}X^-$, thereby forming the desired imidazolidinone salt via ion exchange. A wide variety of salts may be used for this latter purpose, and the cation $M^{+q}$ can be virtually any cation, although q is generally 1, 2 or 3. Suitable M elements are typically chosen from Groups 2 to 13 of the Periodic Table of the Elements, but M may also be a polyatomic cation such as the ammonium ion $NH_4^+$. It should also be noted that the imidazolidinone salt can be prepared with two or more different Brönsted acids or metal salts, thereby forming a mixture of imidazolidinone salts, i.e., salts containing different anions $X^-$.

Further information on these catalysts may be found in U.S. Pat. No. 6,307,057 to MacMillan and Ahrendt for "Acid Addition Salts of Imidazolidinones as Reaction Catalysts," issued Oct. 23, 2001, the disclosure of which is incorporated by reference in its entirety.

Any of the reactions herein can be carried out on a solid support, using solid phase synthesis techniques. Solid-phase synthesis enables implementation of the present reaction in combinatorial chemistry processes, wherein an array or "matrix" of reactions are conducted in parallel on a single substrate. In such a case, the catalyst itself can be bound either directly or indirectly to the surface of a solid substrate, if indirectly, through a cleavable or noncleavable linker. Any solid support may be used. Typical substrates are those conventionally used in solid phase chemistry and which allow for chemical synthesis thereon. The only limitation upon the materials useful for constructing substrates is that they must be compatible with the reaction conditions to which they are exposed. Suitable substrates useful in practicing the methods of the invention include, but are not limited to, organic and inorganic polymers (e.g., polyethylene, polypropylene, polystyrene, polytetrafluoroethylene), metal oxides (e.g., silica, alumina), mixed metal oxides, metal halides (e.g., magnesium chloride), minerals, quartz, zeolites, and the like. Other substrate materials will be apparent to those of skill in the art.

Process conditions: The catalytic fluorination reaction of the invention is generally carried out in a solvent, typically a polar organic solvent, although the specific solvent will depend, of course, on the nature of the reactants, i.e., on any substituents present on the aldehyde(s). Ideally, the solvent selected allows retention and regeneration of the catalyst and removal of the reaction product following completion of the reaction. Examples of suitable solvents include, without limitation, acetone, tetrahydrofuran, chloroform, ethyl acetate, dioxane, acetonitrile, and dimethylsulfoxide. The reaction may be carried out in batch, semi-continuously or continuously, in air or an inert atmosphere, at autogenous pressure or higher, depending, for example, on the nature of the catalyst composition and reactants used. The reaction temperature will generally be in the range of about $-100°$ C. to $100°$ C., preferably in the range of about $-90°$ C. to $50°$ C. Lower temperatures, in the range of about $0°$ C. to about $10°$ C., generally result in a higher yield and greater enantioselectivity, although good yields and ee's greater than 95% are seen at ambient temperature (on the order of $25°$ C.) as well. The amount of catalyst is generally in the range of about 0.1 mole % to 1 stoichiometric equivalent, preferably in the range of about 1 mol % to 20 mole %.

It will be appreciated by those skilled in the art of catalysis that the aforementioned process conditions may vary depending on the particular substrate, fluorination reagent, and catalyst, as well as the equipment used. Generally, the reaction product is obtained after completion of the reaction, wherein an optional extraction and/or catalyst recovery step and/or drying is followed by concentration or distillation to give the crude product and purification, e.g., by chromatography, sublimation, precipitation, extraction, crystallization with optional seeding and/or co-crystallization aids. Alternatively, the reaction product—i.e., the fluorinated aldehyde—may be immediately subjected to further reaction without first being isolated and purified.

It is to be understood that while the invention has been described in conjunction with the preferred specific embodiments thereof, that the description above as well as the examples that follow are intended to illustrate and not limit the scope of the invention. Other aspects, advantages, and modifications within the scope of the invention will be apparent to those skilled in the art to which the invention pertains.

EXPERIMENTAL

In the following examples, efforts have been made to ensure accuracy with respect to numbers used (e.g., amounts, temperature, etc.) but some experimental error and deviation should be accounted for. Unless indicated otherwise, temperature is in degrees C. and pressure is at or near atmospheric.

Commercial reagents were purified prior to use following the guidelines of Perrin and Armarego, *Purification of Laboratory Chemicals*, Fourth Edition (Oxford, Butterworth-Heinemann, 1996). Organic solutions were concentrated under reduced pressure on a Büchi rotary evaporator using an ice-water bath. Chromatographic purification of products was accomplished using forced-flow chromatography on ICN 60 230-400 or Davisil® Silica Gel 200-425 mesh according to the method of Still et al. (1978) *J. Org. Chem.* 43:2923. Thin-layer chromatography (TLC) was performed on EM Reagents 0.25 mm silica gel 60-F plates. Visualization of the developed chromatogram was performed by fluorescence quenching using permanganate stain. High performance liquid chromatography (HPLC) and gas liquid chromatography (GLC) assays to determine enantiomeric excess were developed using racemic samples.

$^1$H and $^{13}$C NMR spectra were recorded on a Varian Mercury 300 spectrometer (300 MHz, 75 MHz, and 282 MHz, respectively), and are internally referenced to residual protio solvent signals. Data for $^1$H NMR are reported as follows: chemical shift (δ ppm), multiplicity (s=singlet, d=doublet, t=triplet, q=quartet, m=multiplet, br=broad), coupling constant (Hz), integration, and assignment. Data for $^{13}$C NMR are reported in terms of chemical shift (δ ppm). IR spectra were recorded on a Perkin Elmer Paragon Spectrum BX FT-IR and are reported in terms of frequency of absorption (cm$^{-1}$). Mass spectra were obtained from the California Institute of Technology Mass Spectral facility. GLC was performed on Hewlett-Packard 6850 Series gas chromatographs equipped with a split-mode capillary injection system and flame ionization detectors using a Macherey-Nagel Hydrodex-B-TBDAc (50 m×0.25 mm) as noted. HPLC was performed on Hewlett-Packard 1100 Series chromatographs using a Chiralcel column (25 mm) and OJ guard (5 cm) as noted.

General Procedure for the α-Fluorination of Aldehydes:

To a 25 mL round-bottom flask equipped with a magnetic stir bar and charged with (R)-5-benzyl-2,2,3,-trimethylimidazolidin-4-one dichloroacetic acid (DCA) salt (1) (139 mg, 0.400 mmol) and N-fluorobenzenesulfonimide (3.15 g, 10.0 mmol) was added tetrahydrofuran (THF) (9.0 mL) and isopropanol (iPrOH) (1.0 mL). The mixture was stirred at room temperature until homogeneous, and then cooled to −10° C. The aldehyde substrate (2.0 mmol) was added and the reaction mixture stirred 12 h. The reaction was cooled to −78° C., diluted with 10 mL diethyl ether (Et$_2$O), and filtered through a pad of Davisil® Silica Gel, eluting with Et$_2$O. Dimethyl sulfide (Me$_2$S) (5.0 mL) was added forming a white precipitate. The resulting mixture was washed with saturated sodium bicarbonate (NaHCO$_3$) (3×150 mL) and brine (1×150 mL), and dried over magnesium sulfate (MgSO$_4$), filtered, and concentrated in vacuo. The resulting oil was dissolved in methylene chloride (CH$_2$Cl$_2$) (12 mL) and ethanol (EtOH) (8 mL), and sodium borohydride (NaBH$_4$) (189 mg, 5.0 mmol) was added. After 30 min. the reaction was cooled to 0° C. and saturated ammonium chloride (NH$_4$Cl) (150 mL) was added. The mixture was warmed to room temperature and stirred vigorously 1 h. The cloudy suspension was allowed to separate and 75 mL of CH$_2$Cl$_2$ was added. The solution was extracted with CH$_2$Cl$_2$ (3×100 mL) and the combined organics washed with saturated NaHCO$_3$ (3×150 mL) and brine (1×150 mL), dried over sodium sulfate (Na$_2$SO$_4$), filtered, and concentrated in vacuo. Purification of the resulting oil by forced flow chromatography afforded the title compounds. The enantioselectivity was determined either by chiral GLC analysis, or chiral HPLC analysis after acylation of the alcohol with 2-naphthoylchloride.

Initially, the general procedure was repeated with two other potential catalysts, L-proline and the imidazolidinone (3), and with other solvents (acetonitrile, ethyl acetate, acetone, CHCl$_3$, and tetrahydrofuran). The percent of aldehyde substrate converted, along with the determined ee, are set forth in Table 1. As may be seen in the table, the organocatalytic α-fluorination method of the invention could be carried out with a variety of catalysts and solvents; however, relatively poor selectivities were observed with L-proline and imidazolidinone 3 (Table 1, entries 1 and 2, ≦63% ee). In contrast, exposure of cyclohexylacetaldehyde to NFSI in the presence of imidazolidinone 1 lead to the desired α-fluoroaldehyde adduct with excellent levels of enantiocontrol (entry 3, 98% ee). A survey of reaction media with catalyst 1 reveals that a number of solvents (in combination with 10% i-PrOH at −10° C.) may be utilized without significant loss in asymmetric induction or reaction efficiency (entries 3-7). The carbonyl-containing solvents (e.g. acetone) were found not to sequester the catalyst or electrophilic fluorination reagent to any detectable extent (entry 6, 89% conversion, 97% ee). The impact of temperature on enantioselectivity was minimal (cf. entries 3 and 9); however, improved conversion was observed at −10° C. (entry 9). The catalytic conditions of entry 9, which gave rise to the highest levels of induction and efficiency (i.e., using amine salt 1 in THF-i-PrOH at −10° C. gave (R)-2-fluorocyclohexylacetaldehyde in 98% ee and 98% conversion, were selected for the further experimental work detailed in Examples 1-9.

TABLE 1

| entry | catalyst | solvent | temp(° C.) | time (h) | % conversion | % ee |
|---|---|---|---|---|---|---|
| 1 | L-proline | THF | 23 | 4 | 79 | 26 |
| 2 | 3 | THF | 23 | 0.3 | 96 | 63 |
| 3 | 1 | THF | 23 | 0.5 | 73 | 98 |
| 4 | 1 | CH$_3$CN | 23 | 3 | 75 | 96 |
| 5 | 1 | EtOAc | 23 | 0.5 | 84 | 96 |
| 6 | 1 | acetone | 23 | 1 | 89 | 97 |
| 7 | 1 | CHCl$_3$ | 23 | 1 | 73 | 96 |
| 8 | 1 | THF | 4 | 6 | 97 | 98 |
| 9 | 1 | THF | −10 | 12 | 98 | 98 |

The enantioselective fluorination reaction was then carried out using a variety of different aldehydes substituted with a wide range of functional groups, including olefins, esters, amines, carbamates, and aryl rings, as described in Examples 1-9.

Starting Materials for Examples 1-9:

Ethyl 5-formylpentanoate: To a flask containing ethyl 6-hydroxyhexanoate (4.07 mL, 25.0 mmol) in CH$_2$Cl$_2$ (25 mL) was added TEMPO (391 mg, 2.50 mmol) followed by iodobenzene diacetate (8.86 g, 27.5 mmol). The reaction was stirred 2 hours and then diluted with CH$_2$Cl$_2$ (100 mL). Saturated aqueous solution of Na$_2$S$_2$O$_3$ (100 mL) was added and extracted with CH$_2$Cl$_2$ (3×50 mL). The combined organics were washed with saturated aqueous NaHCO$_3$ (150 mL) and brine (150 mL), dried over Na$_2$SO$_4$, and concentrated in vacuo. The resulting residue was purified by silica gel chromatography (20-40% Et$_2$O/pentanes) to provide the title compound, which was identical to the reported literature compound. (See: Taber, D. F.; Teng, D. (2002) *J. Org. Chem.*, 67: 1607.)

tert-Butyl 4-(formylmethyl)piperidine-1-carboxylate: To a flask containing tert-butyl 4-(2 hydroxyethyl)piperidine-1-carboxylate (4.4 g, 19.2 mmol) in $CH_2Cl_2$ (20 mL) was added TEMPO (300 mg, 1.92 mmol) followed by iodobenzene diacetate (6.8 g, 21.1 mmol). The reaction was stirred 3 hours and then diluted with $CH_2Cl_2$ (100 mL). Saturated aqueous solution of $Na_2S_2O_3$ (100 mL) was added and extracted with $CH_2Cl_2$ (3×50 mL). The combined organics were washed with saturated aqueous $NaHCO_3$ (150 mL) and brine (150 mL), dried over $Na_2SO_4$, and concentrated in vacuo. The resulting residue was purified by silica gel chromatography (40-70% $Et_2O$/pentanes) to provide the title compound, which was identical to the reported literature compound (see Sato et al. (2001) *Heterocycle* 54: 747). $^{13}C$ NMR (75 MHz, $CDCl_3$) δ 201.5, 154.7, 79.4, 50.3, 43.7, 31.9, 30.6, 28.4.

Adamantyl acetaldehyde: To a flask containing 2-adamantyl-1-ethanol (5 g, 27.7 mmol) in $CH_2Cl_2$ (28 mL) was added TEMPO (433 mg, 2.77 mmol) followed by iodobenzene diacetate (9.8 g, 30.5 mmol). The reaction was stirred 1 hour and then diluted with $CH_2Cl_2$ (100 mL). Saturated aqueous solution of $Na_2S_2O_3$ (100 mL) was added and extracted with $CH_2Cl_2$ (3×50 mL). The combined organics were washed with saturated aqueous $NaHCO_3$ (150 mL) and brine (150 mL), dried over $Na_2SO_4$, and concentrated in vacuo. The resulting residue was purified by silica gel chromatography (5% $Et_2O$/pentanes) to provide the title compound, which was identical to the reported literature compound (see Luly et al. (1987) *J. Org. Chem.* 52: 1487).

EXAMPLE 1

(R)-2-Fluoro-1-undecanol (Table 2, entry 1): Prepared according to the general procedure from undecanal (411 μL, 2.00 mmol) to afford a colorless oil. Purification on silica gel (10-50% $Et_2O$/Pentanes) afforded (R)-2-fluoro-1-undecanol as a colorless solid (261 mg, 70% yield, 94% ee). IR (film) 3271 3171, 2954, 2914, 2848, 1470, 1071, 842.7 $cm^{-1}$; $^1H$ NMR (300 MHz, $CDCl_3$), δ 4.56 (dm, J=46.8 Hz, 1H, FCH), δ 3.59-3.77 (m, 2H, $OCH_2$), δ 1.89 (s, 1H, —OH), 1.20-1.78 (m, 16H, $(CH_2)_8$), δ 0.88 (t, J=6.9 Hz, 3H, $CH_3$); $^{13}C$ NMR (75 MHz, $CDCl_3$) δ; 96.3 (d, J=166.3 Hz), 65.1 (d, J=21.3 Hz), 31.9, 30.9 (d, J=20.3 Hz), 29.5, 29.4 (d, J=3 Hz), 29.3, 24.9, 24.9, 22.7, 14.1. $^{19}F$ NMR (282 MHz, $CDCl_3$) δ: −189.6 (m). HRMS (EI+) exact mass calculated for [M−H]+ ($C_{11}H_{22}FO$) requires m/z 189.1655, found m/z 189.1660. $[α]_D$=7.6 (c=1.0, $CHCl_3$). ($[α]_D$=−8.6 (c=2.0, $Et_2O$) for (S)-2-fluoro-1-decanol and $[α]_D$=−7.2 (c=2.0, $Et_2O$) for (S)-2-fluoro-1-dodecanol (Nohira et al., Japanese Patent No. 62093248 (1987)). Enantiopurity was determined by chiral HPLC analysis of the 2-naphthoyl derivative (Chiralcel®OJ Isocratic 3% i-PrOH/Hexanes). $t_R$(major)=11.4 min. $t_R$(minor)=15.0 min.

EXAMPLE 2

(R)-2-Fluoroundec-10-en-1-ol (Table 2, entry 2): Prepared according to the general procedure from undec-10-enal (416 μL, 2.00 mmol) to afford a colorless oil. Purification on Davisil® silica gel (10-20% EtOAc/Pentanes) afforded (R)-2-fluoroundec-10-en-1-ol as a colorless solid (296 mg, 79% yield, 94% ee). IR (film) 3214, 2918, 2848, 1641, 1460, 1348, 1073, 990.7, 914.2, 837.8, 806.0, 757.8, 724.4, 668.1 $cm^{-1}$; $^1H$ NMR (300 MHz, $CDCl_3$), δ 5.74-5.87 (m, 1H, $CH_2CH=CH_2$), δ 4.90-5.03 (m, 2H, $CH_2CH=CH_2$), δ 4.57 (dm, 1H, J=50.7 Hz, FCH); δ 3.60-3.80 (m, 2H, $OCH_2$), δ 2.03 (q, 2H, J=14.1, and 7.5 Hz, $CH_2CH=CH_2$), δ 1.83 (t, 1H, J=6.6 Hz, —OH), 1.26-1.76 (m, 12H, $FCH(CH_2)_6$); $^{13}C$ NMR (75 MHz, $CDCl_3$) δ; 139.1, 114.2, 94.8 (d, J=166.5 Hz), 65.1 (d, J=21.8 Hz), 31.7, 30.9 (d, J=20.0 Hz), 29.3, 29.3, 29.0, 28.8, 24.9 (d, J=3 Hz). $^{19}F$ NMR (282 MHz, $CDCl_3$) δ: −189.6 (m). HRMS (EI+) exact mass calculated for [M+•]+ ($C_1H_{21}FO$) requires m/z 188.1576, found m/z 188.1575. $[α]_D$=8.1 (c=1.0, $CHCl_3$). Enantiopurity was determined by chiral HPLC analysis of the 2-naphthoyl derivative (Chiralcel®OJ Isocratic 3% i-PrOH/Hexanes). $t_R$(major)=15.7 min. $t_R$(minor)=22.7 min.

EXAMPLE 3

(R)-(Z)-2-Fluorodec-7-en-1-ol (Table 2, entry 3): Prepared according to the general procedure from (Z)-dec-7-enal (366 μL, 2.00 mmol) to afford a yellow oil. Purification on silica gel (5-20% EtOAc/Pentanes) afforded (R)-(Z)-2-fluorodec-7-en-1-ol as a pale yellow liquid (283 mg, 81% yield, 94% ee). IR (film) 3369, 3006, 2935, 2861, 1462, 1376, 1172, 1056, 843.1 $cm^{-}$; $^1H$ NMR (300 MHz, $CDCl_3$) δ 5.26-5.42 (m, 2H, $CH_2CH=HCCH_2$), δ 4.56 (dm, 1H, J=50.5 Hz, FCH), δ 3.62-3.76 (m, 2H, $OCH_2$), δ 1.98-2.10 (m, 4H, $CH_2CH=HCCH_2$), δ 1.89 (t, 1H, J=6.4 Hz, —OH), δ 1.32-1.74 (m, 6H, $CFH(CH_2)_3$), δ 0.95 (t, 3H, J=7.4 Hz, $CH_3$); $^{13}C$ NMR (75 MHz, $CDCl_3$) δ: 132.0, 128.7, 94.7 (d, J=166.5 Hz), 65.1 (d, J=21.3 Hz), 30.9 (d, J=20.0 Hz), 29.5, 26.8, 24.5 (d, J=5.0 Hz), 20.5, 14.3. $^{19}F$ NMR (282 MHz, $CDCl_3$) δ: −189.6 (m). HRMS (EI+) exact mass calculated for [M+•]+ (C10H19FO) requires m/z 174.1420, found m/z 174.1421. $[α]_D$=5.6 (c=1.0, $CHCl_3$). Enantiopurity was determined by chiral HPLC analysis of the 2-naphthoyl derivative (Chiralcel®OJ Isocratic 0.5% i-PrOH/Hexanes). $t_R$(major)=32.2 min. $t_R$(minor)=51.9 min.

EXAMPLE 4

(R)-Ethyl 5-fluoro-6-hydroxyhexanoate (Table 2, entry 4): Prepared according to the general procedure from ethyl 5-formylpentanoate (319 μL, 2.00 mmol) to afford a colorless oil. Purification on silica gel (20-40% EtOAc/Pentanes) afforded (R)-ethyl 5-fluoro-6-hydroxyhexanoate as a colorless liquid (274 mg, 77% yield, 91% ee). IR (film) 3436, 2942, 1733, 1453, 1376, 1165, 1096, 1065, 1035, 849.9, 772.2 $cm^{-1}$; $^1H$ NMR (300 MHz, $CDCl_3$) δ 4.57 (dm, 1H, J=49.4, FCH), δ 4.12 (q, 2H, J=7.2 Hz, $CO_2CH_2$), δ 3.60-3.78 (m, 2H, $OCH_2$), δ 2.34 (t, 2H, J=7.0 Hz, $CH_2CO_2$), δ 2.04 (s, 1H, —OH), δ 1.50-1.88 (m, 4H, $CFH(CH_2)_2$), δ 1.24 (t, 3H, J=7.2 Hz, $CH_3$); $^{13}C$ NMR (75 MHz, $CDCl_3$) δ: 173.3, 94.2 (d, J=167.3 Hz), 64.8 (d, J=21.7 Hz), 60.4, 33.8, 30.2 (d, J=20.6 Hz), 20.4 (d, J=5.0 Hz), 14.2. $^{19}F$ NMR (282 MHz, $CDCl_3$) δ; −190.3 (m). HRMS (EI+) exact mass calculated for [M+H]+ ($C_8H_{16}FO_3$) requires m/z 179.1084, found m/z 179.1083. $[α]_D$=−5.1 (c=1.0, $CHCl_3$). Enantiopurity was determined by chiral HPLC analysis of the 2-naphthoyl derivative (Chiralcel®OJ Isocratic 10% EtOH/Hexanes). $t_R$(major)=47.7 min. $t_R$(minor)=68.7 min.

EXAMPLE 5

(S)-2-Cyclohexyl-2-fluoro-1-ethanol (Table 2, entry 5): Prepared according to the general procedure from 2-cyclohexyl-1-ethanol (291 μL, 2.00 mmol) to afford a colorless oil. Purification on silica gel (10-50% $Et_2O$/Pentanes)

afforded (R)-2-cyclohexyl-2-fluoro-1-ethanol as a colorless liquid (282 mg, 96% yield, 99% ee). IR (film) 3369, 2928, 2854, 1450, 1091, 1074, 1058, 1024, 977.7, 891.8, 858.9, 837.7 cm$^{-1}$; $^1$H NMR (300 MHz, CDCl$_3$) δ 4.28 (dm, 1H, J=49.2 Hz, FCH), δ 3.68-3.81 (m, 2H, OCH$_2$), δ 1.83-1.94 (m, 2H, CH$_2$), δ 1.56-1.84 (m, 5H, (CH$_2$)$_2$ and OH), δ 0.99-1.34 (m, 5H, (CH$_2$)$_2$ and CFHCH); $^{13}$C NMR (75 MHz, CDCl$_3$) δ: 98.4 (d, J=168.3 Hz), 63.2 (d, J=26.2 Hz), 30.2 (d, J=19.1 Hz), 28.1 (dd, J=22.7, 6.0 Hz), 26.1, 25.7 (d, J=12.6 Hz). $^{19}$F NMR (282 MHz, CDCl$_3$) δ: −194.7 (m). HRMS (EI+) exact mass calculated for [M+•]$^+$ (C$_8$H$_{15}$FO) requires m/z 146.1107, found m/z 146.1101. [α]$_D$=−0.26 (c=1.0, EtOH). Enantiopurity was determined by GLC using a Macherey-Nagel Hydrodex-BTBDAc (50 m×0.25 mm) column (100° C. isotherm); (R) isomer t$_r$=79.9 min and (S) isomer t$_r$=88.8 mm.

EXAMPLE 6

(R)-tert-Butyl 4-(1-fluoro-2-hydroxyethyl)piperidine-1-carboxylate (Table 2, entry 6): Prepared according to the general procedure from tert-butyl 4-(formylmethyl)piperidine-1-carboxylate (455 mg, 2.00 mmol) to afford a colorless oil. Purification on silica gel (25-50% EtOAc/Pentanes) afforded (R)-tert-butyl-4-(1-fluoro-2-hydroxyethyl)piperidine-1-carboxylate as a colorless oil (422 mg, 85% yield, 98% ee). IR (film) 3430, 2930, 1692, 1671, 1427, 1365, 1283, 1241, 1170, 1084, 1040, 971.6, 940.0, 857.2, 770.1 cm$^{-1}$; $^1$H NMR (300 MHz, CDCl$_3$) δ 4.06-4.40 (m, 3H, N(CH$_a$CH$_b$)$_2$, and FCH), δ 3.69-3.83 (m, 2H, OCH$_2$), δ 2.68 (br m, 2H, N(CH$_a$CH$_b$)$_2$), δ2.01 (t, 1H, J=6.0 Hz, —OH), δ 1.80-1.87 (m, 2H, (CH$_a$CH$_b$CH$_2$)$_2$N), δ 1.51-1.67 (m, 1H, CHFCH), δ 1.44 (s, 9H, (CH3)3), δ 1.22-1.32 (m, 2H, (CH$_a$CH$_b$CH$_2$)$_2$N); $^{13}$C NMR (75 MHz, CDCl$_3$) δ: 154.7, 97.3 (d, J=170.0 Hz), 79.5, 62.8 (d, J=22.0 Hz), 60.4, 37.1 (d, J=19.7 Hz), 28.4, 27.3, 27.3; $^{19}$F NMR (282 MHz, CDCl$_3$) δ: −194.5 (bs). HRMS (EI+) exact mass calculated for [M+•]$^+$ (C$_{12}$H$_{22}$FNO$_3$) requires m/z 247.1584, found m/z 247.1587. [α]$_D$=3.0 (c=1.0, CHCl$_3$). Enantiopurity was determined by chiral HPLC analysis of the 2-naphthoyl derivative (Chiralcel®OJ Isocratic 10% EtOH/Hexanes). t$_R$(major)=28.3 min. t$_R$(minor)=41.1 min.

EXAMPLE 7

(R)-2-Fluoro-2-phenyl-1-ethanol (Table 2, entry 7): Prepared according to the general procedure from phenylacetaldehyde (234 μL, 2.00 mmol) to afford a colorless oil. Purification on silica gel (10-50% Et$_2$O/Pentanes) afforded (R)-2-fluoro-2-phenyl-1-ethanol as a colorless liquid (152 mg, 54% yield, 99% ee), which matched literature data (see Watanabe et al. (1986) J. Fluorine Chem. 31: 247.) IR (film) 3369, 1496, 1454, 1078, 1043, 877.9, 834.2, 757.3, 698.8 cm$^{-1}$; $^1$H NMR (300 MHz, CDCl$_3$) δ 7.32-7.41 (m, 5H, C$_6$H$_5$), δ 5.57 (ddd, 1H, J=48.9, 7.7, and 5.2 Hz, FCH), δ 3.73-4.01 (m, 2H, OCH$_2$), δ 2.18 (dd, 1H, —OH); $^{13}$C NMR (75 MHz, CDCl$_3$) δ: 136.3 (d, J=19.6 Hz), 128.8 (d, J=2.0 Hz), 128.6, 125.7 (d, J=6.9 Hz), 94.8 (d, J=170.9 Hz), 66.6 (d, J=24.5 Hz); $^{19}$F NMR (282 MHz, CDCl$_3$) δ: −187.0 (ddd, J=12.8, 7.6, 4.5 Hz). HRMS (EI+) exact mass calculated for [M+•]$^+$ (C$_8$H$_9$FO) requires m/z 140.0637, found m/z 140.0636. [α]$_D$=−47.9 (c=1.0, CHCl$_3$). Reported rotation for the S-enantiomer [α]$_D$=52.5 (c=1.1, CHCl$_3$). (See: Davis, F. A.; Han, W. (1992) Tetrahedron Lett. 33: 1153.) Enantiopurity was determined by GLC using a Macherey-Nagel Hydrodex-B-TBDAc (50 m×0.25 mm) column (110° C. isotherm); (R) isomer t$_r$=57.1 min and (S) isomer t$_r$=59.4 min.

EXAMPLE 8

(R)-2-Fluoro-3-phenyl-1-propanol (Table 2, entry 8): Prepared according to the general procedure from hydrocinnamaldehyde (263 μL, 2.00 mmol) to afford a colorless oil. Purification on silica gel (10-40% Et$_2$O/Pentanes) afforded (R)-2-fluoro-3-phenyl-1-propanol as a colorless liquid (218 mg, 71% yield, 96% ee), which matched literature data. (See: Takeuchi, Y.; Nagata, K.; Koizumi, T. (1989) J. Org. Chem. 54, 5453.) IR (film) 3369, 3029, 2932, 1497, 1455, 1052, 904.3, 835.6, 745.7, 700.0 cm$^{-1}$; $^1$H NMR (300 MHz, CDCl$_3$) δ 7.21-7.36 (m, 5H, C$_6$H$_5$), δ 4.78 (dm, 1H, J=48.6 Hz, FCH), δ 3.60-3.85 (m, 2H, OCH$_2$), δ 2.87-3.10 (m, 2H, PhCH$_2$), δ 1.97 (t, 1H, J=6.1 Hz, —OH); $^{13}$C NMR (75 MHz, CDCl$_3$) δ: 136.3 (d, J=6.0 Hz), 129.3, 128.6, 126.8, 95.6 (d, J=170.6 Hz), 64.1 (d, J=21.3 Hz), 37.4 (d, J=20.0 Hz); $^{19}$F NMR (282 MHz, CDCl$_3$) δ: −187.6 (m). HRMS (EI+) exact mass calculated for [M+•]$^+$ (C$_9$H$_{11}$FO) requires m/z 154.0794, found m/z 194.0797. [α]$_D$=16.7 (c=1.0, CHCl$_3$). Reported rotation for the S-enantiomer [α]$_D$=−17.6 (c=1.7, CHCl$_3$). (See: Davis, F. A.; Han, W. (1992) Tetrahedron Lett. 33: 1153.) Enantiopurity was determined by GLC using a Macherey-Nagel Hydrodex-B-TBDAc (50 m×0.25 mm) column (120° C. isotherm); (R) isomer t$_r$=76.1 min and (S) isomer t$_r$=84.3 min.

EXAMPLE 9

(R)-2-Adamantyl-2-fluoro-1-ethanol (Table 2, entry 9): Prepared according to the general procedure from adamantyl acetaldehyde (334 μL, 2.00 mmol) to afford a colorless oil. Purification on silica gel (5-20% EtOAc/Pentanes) afforded (R)-2-adamantyl-2-fluoro-1-ethanol as a colorless solid (326 mg, 82% yield, 98% ee). IR (film) 3306, 2903, 2850, 1451, 1348, 1087, 1058, 1028, 989.3, 859.0 cm$^{-1}$; $^1$H NMR (300 MHz, CDCl$_3$) δ 4.07 (ddd, 1H, J=49.7, 7.8, and 5.1 Hz, FCH), δ 3.62-3.88 (m, 2H, OCH$_2$), δ1.99 (s, 3H, CH(CH$_2$)$_3$) δ 1.54-1.84 (m, 13H, —OH, (CH$_2$)$_6$); $^{13}$C NMR (75 MHz, CDCl$_3$) δ: 101.8 (d, J=170.3 Hz), 61.3 (d, J=22.3 Hz), 37.7 (d, J=4.1 Hz), 36.9, 35.4 (d, J=19.6 Hz), 27.9 (J=0.6 Hz); $^{19}$F NMR (282 MHz, CDCl$_3$) δ: −203.1 (ddd, J=48.5, 34.2, 17.2 Hz). HRMS (EI+) exact mass calculated for [M+•]$^+$ (C$_{12}$H$_{19}$FO) requires m/z 198.1420, found m/z 198.1417. [α]$_D$=−9.5 (c=1.0, CHCl$_3$). Enantiopurity was determined by chiral HPLC analysis of the 2-naphthoyl derivative (Chiralcel®OJ Isocratic 3% iPrOH/Hexanes). t$_R$(major)=20.8 min. t$_R$(minor)=26.5 min.

The data set forth in Table 2 indicates that the enantioselective fluorination reaction of the invention can be carried out with aldehydes substituted with a wide range of functional groups, including olefins, esters, amines, carbamates, and aryl rings (see Table 2, entries 2-4,6-8: 91-99% ee). Moreover, extensive variation in the steric demands of the aldehyde substituent can be realized (Table 2, entries 1, 5, 7-9; R=nonyl, cyclohexyl, Bn, Ph, adamantyl) without loss in efficiency or enantiocontrol (54-96% yield, 94-99% ee). A catalyst exposure study revealed that product epimerization was not observed over the indicated reaction time for any of the reactions of Table 2. These results serve to illustrate the remarkable capacity of imidazolidinone 1 to successfully differentiate between the aldehyde α-methylene substrates and the α-fluoro aldehyde products. A defining example of such chemoselectivity was found in the production of (R)-2-fluorophenylacetaldehyde, a highly enolizable aldehyde that is configurationally stable under the mild organocatalytic conditions used in conjunction with the reaction of the present invention (Table 2, entry 7, 99% ee).

TABLE 2

Enantioselective α-Fluorination: Substrate Scope aldehyde (H-C(=O)-CH2-R) + Ph-S(O2)-N(F)-S(O2)-Ph → (1) 20 mol% 1, THF, i-PrOH, -10° C. (2) NaBH4, CH2Cl2 → HO-CH2-CHF-R

| entry | product | time (h) | % yield | % ee[b] |
|---|---|---|---|---|
| 1 | HO-CH2-CHF-(CH2)6-Me | 10 | 70 | 94 |
| 2 | HO-CH2-CHF-(CH2)6-CH=CH2 | 10 | 79 | 94 |
| 3 | HO-CH2-CHF-(CH2)3-CH=CH-Et (cis) | 10 | 81 | 94 |
| 4 | HO-CH2-CHF-(CH2)2-C(=O)-OEt | 12 | 77 | 91 |
| 5 | HO-CH2-CHF-cyclohexyl | 12 | 96 | 99[b] |
| 6 | HO-CH2-CHF-(4-piperidyl-NBOC) | 12 | 85 | 92 |
| 7 | HO-CH2-CHF-Ph | 10 | 54 | 99[b] |
| 8 | HO-CH2-CHF-CH2-Ph | 12 | 71 | 99[b] |
| 9 | HO-CH2-CHF-adamantyl | 12 | 82 | 98 |

Last, the effect of catalyst loading on reaction efficiency was evaluated, with the results set forth in Table 3. Catalyst loadings as low as 2.5 mol % were utilized without loss in enantiocontrol (Table 3, entry 7: 98% ee). In terms of operational convenience, the use of 20 mol % imidazolidinone 1 at −10° C. or of 5-10 mol % of 1 at 4° C. ensures high levels of reaction efficiency and enantioselectivity while expedient reaction times were maintained (Table 3, entry 4, 4° C. 10 mol % 1, 97% conversion, 98% ee, 8 h; entry 6, 4° C., 5 mol % 1, 95% conversion, 98% ee, 25 h).

TABLE 3

Effect of Catalyst Loading on Aldehyde α-Fluorination cyclohexyl-CH2-CH(=O)H + NFSI →(catalyst, THF, i-PrOH)→ cyclohexyl-CHF-CH(=O)H

| entry | mol % caralyst 2 | Temp ° C. | time | % conv.[a] | % ee[b] |
|---|---|---|---|---|---|
| 1 | 20 | +23 | 20 min | 73 | 98 |
| 2 | 20 | −10 | 12 h | 98 | 98 |
| 3 | 10 | +23 | 3 h | 78 | 98 |
| 4 | 10 | −10 | 8 h | 97 | 98 |
| 5 | 5 | +23 | 3 h | 66 | 98 |
| 6 | 5 | +4 | 25 h | 95 | 98 |
| 7 | 2.5 | +23 | 12 h | 79 | 98 |

The invention thus provides a mild, operationally simple, organocatalytic protocol that allows direct access to carbon-fluorine stereogenicity in a wide variety of structural contexts using readily available catalysts and an electrophilic fluorine source.

We claim:

1. A method for the enantioselective fluorination of an aldehyde, comprising contacting an enolizable aldehyde with a fluorination reagent in the presence of a catalytically effective amount of a nonmetallic chiral catalyst containing a Group 15 or Group 16 heteroatom.

2. The method of claim 1, wherein the enolizable aldehyde has the structure of formula (I)

in which $R^1$ and $R^2$ are independently selected from hydrogen, hydrocarbyl, substituted hydrocarbyl, heteroatom-containing hydrocarbyl, substituted heteroatom-containing hydrocarbyl, and functional groups.

3. The method of claim 2, wherein $R^1$ and $R^2$ are independently selected from hydrogen, $C_1$-$C_{24}$ alkyl, substituted $C_1$-$C_{24}$ alkyl, $C_1$-$C_{24}$ heteroalkyl, substituted $C_1$-$C_{24}$ heteroalkyl, $C_5$-$C_{24}$ aryl, substituted $C_5$-$C_{24}$ aryl, $C_1$-$C_{24}$ heteroaryl, substituted $C_1$-$C_{24}$ heteroaryl, $C_6$-$C_{24}$ aralkyl, substituted $C_6$-$C_{24}$ aralkyl, $C_2$-$C_{24}$ heteroaralkyl, substituted $C_2$-$C_{24}$ heteroaralkyl, hydroxyl, $C_1$-$C_{24}$ alkoxy, sulfhydryl, and amino.

4. The method of claim 3, wherein $R^1$ and $R^2$ are independently selected from hydrogen, $C_1$-$C_{12}$ alkyl, substituted $C_1$-$C_{12}$ alkyl, $C_1$-$C_{12}$ heteroalkyl, substituted $C_1$-$C_{12}$ heteroalkyl, $C_5$-$C_{14}$ aryl, substituted $C_5$-$C_{14}$ aryl, $C_3$-$C_{14}$ heteroaryl, substituted $C_3$-$C_{14}$ heteroaryl, $C_6$-$C_{16}$ aralkyl, substituted $C_6$-$C_{16}$ aralkyl, $C_3$-$C_{16}$ heteroaralkyl, substituted $C_3$-$C_{16}$ heteroaralkyl, hydroxyl, sulfhydryl, and amino.

5. The method of claim 4, wherein $R^2$ is hydrogen.

6. The method of claim 1, wherein the heteroatom of the catalyst is selected from the group consisting of nitrogen, oxygen, sulfur, and phosphorus.

7. The method of claim 6, wherein the heteroatom is nitrogen.

8. The method of claim 7, wherein the catalyst is a secondary amine or an acid addition salt thereof.

9. The method of claim 8, wherein the secondary amine is chiral with respect to an axis, plane or center of asymmetry.

10. The method of claim 9, wherein the secondary amine has the structure of formula (II)

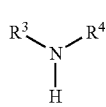

(II)

wherein $R^3$ and $R^4$ are independently selected from the group consisting of hydrocarbyl, substituted hydrocarbyl, heteroatom-containing hydrocarbyl, and substituted heteroatom-containing hydrocarbyl, or are taken together to form a ring, such that the amine is a cyclic secondary amine.

11. The method of claim 10, wherein $R^3$ and $R^4$ are taken together to form a 3- to 15-membered, optionally substituted ring.

12. The method of claim 9, wherein the catalyst is an imidazolidinone salt having the structure of formula (III) or (IV)

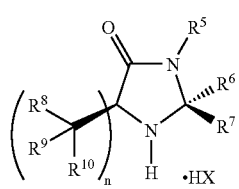

(III)

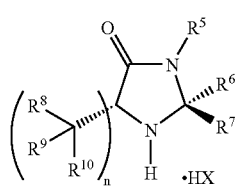

(IV)

wherein:
$R^5$ is selected from hydrocarbyl, substituted hydrocarbyl, heteroatom-containing hydrocarbyl, and substituted heteroatom-containing hydrocarbyl;
$R^6$ and $R^7$ are independently selected from hydrocarbyl, substituted hydrocarbyl, heteroatom-containing hydrocarbyl, substituted heteroatom-containing hydrocarbyl, and functional groups;
$R^8$ is selected from hydrogen, halo, hydroxyl, hydrocarbyl, substituted hydrocarbyl, heteroatom-containing hydrocarbyl, substituted heteroatom-containing hydrocarbyl;
$R^9$ is selected from hydrogen, halo, hydrocarbyl, substituted hydrocarbyl, heteroatom-containing hydrocarbyl, substituted heteroatom-containing hydrocarbyl;

$R^{10}$ is a cyclic group, either unsubstituted or substituted with 1 to 4 non-hydrogen substituents and containing zero to 3 heteroatoms;
HX is a Brönsted acid; and
n is zero or 1,
wherein the imidazolidinone salt is optionally covalently bound, directly or indirectly, to a solid support.

13. The method of claim 12, wherein the imidazolidinone salt has the structure of formula (III).

14. The method of claim 12, wherein the imidazolidinone salt has the structure of formula (IV).

15. The method of claim 12, wherein:
$R^5$ is selected from $C_1$-$C_{12}$ alkyl, substituted $C_1$-$C_{12}$ alkyl, $C_1$-$C_{12}$ heteroalkyl, substitute $C_1$-$C_{12}$ heteroalkyl, $C_5$-$C_{14}$ aryl, substituted $C_5$-$C_{14}$ aryl, $C_3$-$C_{14}$ heteroaryl, substituted $C_3$-$C_{14}$ heteroaryl, $C_6$-$C_{16}$ aralkyl, substituted $C_6$-$C_{16}$ aralkyl, $C_3$-$C_{16}$ heteroaralkyl, and substituted $C_3$-$C_{16}$ heteroaralkyl;
$R^6$ and $R^7$ are selected from $C_1$-$C_{12}$ alkyl and substituted $C_1$-$C_{12}$ alkyl;
n is 1;
$R^8$ and $R^9$ are hydrogen; and
$R^{10}$ is $C_5$-$C_{14}$ aryl.

16. The method of claim 15, wherein $R^5$, $R^6$, and $R^7$ are $C_1$-$C_{12}$ alkyl $R^6$ and $R^7$ are the same, and $R^{10}$ is unsubstituted phenyl.

17. The method of claim 1, wherein the fluorination reagent is an electrophilic fluorination reagent.

18. The method of claim 17, wherein the fluorination reagent is selected from fluorinated diazabicycloalkane compounds and N-fluorobenzenesulfonimides.

19. The method of claim 17, wherein the fluorination reagent is selected from N-fluorobenzenesulfonimide, N-fluoromethanesulfonimide, 1-chloromethyl-4-fluoro-1,4-diazoniabicyclo[2.2.2]octane bis(tetra-fluoroborate), 1-hydroxyl-4-fluoro-1,4-diazoniabicyclo[2.2.2]octane bis(tetrafluoroborate), and N-fluoropyridinium pyridine heptafluorodiborate.

20. A reaction system comprising an enolizable aldehyde, an electrophilic fluorination reagent, and a nonmetallic chiral catalyst comprising an imidazolidinone salt having the structure of formula (III) or (IV)

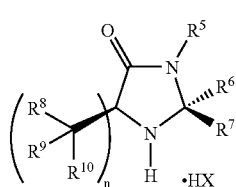

(III)

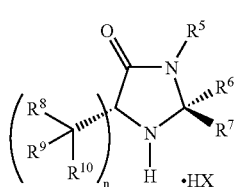

(IV)

wherein:
$R^5$ is selected from hydrocarbyl, substituted hydrocarbyl, heteroatom-containing hydrocarbyl, and substituted heteroatom-containing hydrocarbyl;

$R^6$ and $R^7$ are independently selected from hydrocarbyl, substituted hydrocarbyl, heteroatom-containing hydrocarbyl, substituted heteroatom-containing hydrocarbyl, and functional groups;

$R^8$ is selected from hydrogen, halo, hydroxyl, hydrocarbyl, substituted hydrocarbyl, heteroatom-containing hydrocarbyl, substituted heteroatom-containing hydrocarbyl;

$R^9$ is selected from hydrogen, halo, hydrocarbyl, substituted hydrocarbyl, heteroatom-containing hydrocarbyl, substituted heteroatom-containing hydrocarbyl;

$R^{10}$ is a cyclic group, either unsubstituted or substituted with 1 to 4 non-hydrogen substituents and containing zero to 3 heteroatoms;

HX is a Brönsted acid; and n is zero or 1.

* * * * *